United States Patent [19]

Rawlings et al.

[11] Patent Number: 4,798,201

[45] Date of Patent: * Jan. 17, 1989

[54] SURGICAL ADHESIVE DRESSING

[75] Inventors: David A. Rawlings, Stansted Mountfitchet; William D. Potter, Stortford, both of United Kingdom

[73] Assignee: Smith and Nephew Associated Companies p.l.c., United Kingdom

[*] Notice: The portion of the term of this patent subsequent to Jun. 17, 2003 has been disclaimed.

[21] Appl. No.: 947,613

[22] Filed: Dec. 30, 1986

Related U.S. Application Data

[63] Continuation of Ser. No. 539,098, Oct. 5, 1983, abandoned.

[30] Foreign Application Priority Data

Apr. 13, 1983 [GB] United Kingdom ............... 8309993

[51] Int. Cl.$^4$ .............................................. A61L 15/00
[52] U.S. Cl. ................................... 128/156; 428/195; 428/423.1
[58] Field of Search .................... 128/156; 604/307; 428/423.1, 195

[56] References Cited

U.S. PATENT DOCUMENTS

| | | | |
|---|---|---|---|
| 2,871,218 | 1/1959 | Schollenberger | 525/440 |
| 2,949,443 | 8/1960 | Merriam et al. | 128/156 |
| 3,121,021 | 2/1964 | Copeland | 428/219 |
| 3,483,018 | 12/1969 | Waldman | 428/286 |
| 3,520,949 | 7/1970 | Shepherd et al. | 525/426 |
| 3,526,224 | 6/1967 | Potts | 128/156 |
| 3,579,628 | 5/1971 | Gander | 428/28 |
| 3,645,835 | 2/1972 | Hodgson | 428/195 |
| 3,821,136 | 6/1974 | Hudgin et al. | 527/302 |
| 3,822,238 | 7/1974 | Blair et al. | 528/59 |
| 3,975,350 | 8/1976 | Hudgin et al. | 524/108 |
| 4,061,618 | 12/1977 | Stanley | 260/29.2 TN |
| 4,127,127 | 11/1978 | Wong et al. | 128/130 |
| 4,156,066 | 5/1979 | Gould | 528/73 |
| 4,156,067 | 5/1979 | Gould | 528/73 |
| 4,289,125 | 9/1981 | Hung | 128/156 |
| 4,340,043 | 7/1982 | Seymour | 604/307 |
| 4,413,621 | 11/1983 | McCracken et al. | 128/156 |
| 4,414,970 | 11/1983 | Berry | 128/156 |
| 4,595,001 | 1/1986 | Potter et al. | 128/156 |

FOREIGN PATENT DOCUMENTS

| | | |
|---|---|---|
| 0006714 | 6/1979 | European Pat. Off. . |
| 0028452 | 9/1980 | European Pat. Off. . |
| 0050035 | 10/1981 | European Pat. Off. . |
| 0051935 | 5/1982 | European Pat. Off. . |
| 0072258 | 2/1983 | European Pat. Off. . |
| 0091800 | 10/1983 | European Pat. Off. . |
| 2440380 | 6/1978 | France . |
| 648733 | 10/1951 | United Kingdom . |
| 761840 | 11/1956 | United Kingdom . |
| 83/03549 | 10/1983 | World Int. Prop. O. ......... 128/156 |

*Primary Examiner*—Steven Capella
*Attorney, Agent, or Firm*—Jacobs & Jacobs

[57] ABSTRACT

A surgical dressing is described which consists essentially of a film which carries an adhesive layer for securing the dressing to the body characterized in that (a) the film is continuous and comprises a polymer which in contact with water has a higher MVP than when in contact with moisture vapor but not water; (b) the adhesive layer is adapted to allow access of water to the film when water is in contact with the adhesive layer so that (c) the surgical dressing has an MVP of not less than 2500 g/m$^2$ when the adhesive layer is in contact with water and has an MVP of not more than 2000 g/m$^2$ when the adhesive is in contact with moisture vapor but not water; whereby the dressing is suitable for use on exuding wounds and on non-exuding wounds.

19 Claims, No Drawings

SURGICAL ADHESIVE DRESSING

CROSS-REFERENCE

This is a continuation of Ser. No. 539,098 filed Oct. 5, 1983, now abandoned.

The present invention relates to adhesive dressings for use on the human body. More particularly this invention relates to adhesive surgical dressings suitable for use on both exuding wounds and non-exuding wounds.

Moisture vapour permeable thin films coated with adhesive were disclosed in British Pat. No. 1,280,631 and U.S. Pat. No. 3,645,835 as being suitable for use as surgical dressings. In recent years one such film has come to prominence under the trade mark "Op-Site" and has found use as a surgical dressing, for example for covering burns, donor sites, surgical incisions, intravenous catheter sites and the like. The known dressings have proved useful because they keep out bacteria owing to the microscopically continuous nature of the film and adhesive layer but do not cause maceration of the skin to which it is applied because both the film and the adhesive layer have high moisture vapour permeability (MVP). One problem with presently available high MVP dressings is that the MVP is not high enough for some uses such as covering exuding wounds when an unsightly blister can occur. However it has not been thought practicable simply to increase the MVP of the product overall since this would lead to drying out of some wounds with a consequent reduction in the rate of healing. It has now been discovered that it is possible to alleviate the known disadvantages of conventional surgical dressings by providing dressings which transmit substantially more moisture vapour when in contact with a wetter wound than they do when in contact with a dryer wound.

Accordingly the present invention provides a surgical dressing which consists essentially of a film which carries an adhesive layer for securing the dressing to the body characterised in that (a) the film is continuous and comprises a polymer which in contact with water has a higher MVP than when in contact with moisture vapour but not water (b) the adhesive layer is porous and allows access of water to the film when water is in contact with the adhesive layer so that (c) said surgical dressing has a MVP of not less than 2500 g/m$^2$ when the adhesive layer is in contact with water and has an MVP of not more than 2000 g/m$^2$ when the adhesive is in contact with moisture vapour but not water; whereby the dressing is suitable for use on exuding wounds and on non-exuding wounds.

When used herein with reference to "contact" the term "water" means liquid water (as opposed to moisture vapour) unless otherwise specified. When used herein MVP units are g/m$^2$/24 hrs/37° C./100–10% relative humidity and are generally abbreviated to g/m$^2$.

Suitable test methods for determining the MVP of a dressing or its components are set forth in the Description hereinafter. When MVP values quoted thereinafter are referred to as "wet-MVP" they refer to values obtained with the adhesive face in contact with water and when referred to as "dry-MVP" they refer to values obtained with the adhesive face not in contact with water.

More suitably the dressing of this invention will have a wet-MVP of not less than 3000 g/m$^2$, most suitably will have a wet-MVP of not less than 3200 g/m$^2$ and preferably will have a wet-MVP of not less than 5000 g/m$^2$.

More suitably the dressing of this invention will have a dry-MVP of not more than 1500 g/m$^2$, most suitably will have a dry-MVP of not more than 1400 g/m$^2$ and preferably will have a dry-MVP of not more than 1200 g/m$^2$.

The film used in this invention may comprise any synthetic or modified natural polymer which has a sufficiently higher wet-MVP than dry-MVP to produce the desired MVP parameters in the dressing. The method set out in the Descriptions may be employed to determine whether the film material exibits the desired MVP when in contact with water. Most aptly the film comprises a synthetic polymer although modified natural polymers such as regenerated cellulose or cellulose acetate may be employed if sufficiently plasticised to conform to the movements of the body when adhered thereto. Preferably the synthetic polymer employed is an elastomer so that it readily conforms to the movement of the skin when the dressing is in use.

Most suitably the film used in this invention will be hydrophilic, that is will absorb water when immersed therein. Aptly the film material when hydrated will contain 5% to 50% water (w/w at 20° C.), more aptly from 10% to 40% of water and favourably from 20% to 30% of water.

Suitable hydrophilic film material will include polyurethanes, polyether polyamide block copolymers, polyether polyester block copolymers, cross-linked polyvinyl alcohols, acrylic copolymers, polyamides, regenerated cellulose, cellulose acetate and the like, provided said film material are highly conformable (whether per se or by plasticisation) and that the material used most suitably has the preceeding water contents when hydrated.

The film employed will be a continuous film, that is it will be free of holes (whether microporous or macroporous) which allow the passage of bacteria.

The desirable properties of this invention may be best obtained by employing a film of hydrophilic polyurethane in combination with an adhesive layer adapted to allow access of water to the film when water is presented to the adhesive face of the dressing.

Most suitably the film will be from 15 to 80 microns thick, will more usually be from 20 to 60 microns thick and will preferably be from 25 to 50 microns thick, for example 30, 35 or 40 microns thick.

Aptly the film will be formed from a hydrophilic polyurethane which when hydrated contains from 5% to 50% of water, more aptly from 10% to 40% of water and favourably from 20% to 30% water.

In order to enable visual observation of the wound it is desirable for the film used in this invention to be transparent. This in turn requires that the film should be capable of being self supporting, that is sufficiently coherent when wet or dry to be used without recourse to additional support such as a fabric, for example a gauze, net or the like. It has been found that polyether polyurethanes are particularly suitable for use in the formation of such films. Favoured polyether polyurethanes are essentially free of reactive substituents such as hydroxyl or carboxyl groups. It has been found that certain apt polyurethanes for use in this invention are random polymers containing units derived from diolic compounds and diisocyanates.

Suitable polyurethanes are disclosed in British Patent Specification No. 2093190A at page 3 lines 16 to 74 which are incorporated herein by cross reference.

The adhesive layer present on the body contacting surface of the film is a porous layer which allows access of liquid water to the film. Most suitably the pores will be large in comparison to the thickness of the adhesive layer. Favourably the diameters of the pores are 2 to 3 times the thickness of the adhesive layer. The scanning electron microscope may be used to examine the porous adhesive layer. Most aptly the pores account for 10-50% of the area of the adhesive and preferably 15-40% of the area of the adhesive and most preferably 20-30% of the area of the adhesive. The use of a porous layer in such a manner has been found to be highly beneficial in allowing the desirable variability of MVP to be achieved.

The adhesive is generally employed at a mass per unit area of 20 to 80 g/m², More aptly 20 to 45 g/m² and favourably from 25 to 35 g/m².

The adhesive to normally and preferably applied over the whole operation area of the dressing.

The adhesive is preferably one which itself transmits water vapour, for example one which if present as a film 25 microns thick would have a MVP of at least 300 g/m², more suitably at least 500 g/m² and preferably at least 700 g/m². Such permeabilities are enhanced by using a porous adhesive. Suitably adhesives include polyvinyl ethyl ether adhesive and acrylate surgical adhesives. Preferred adhesive include those described in European Patent Application No. 81300847 (Publication No. 0035399).

The dressings of the invention may be made by any convenient process, for example a film of, for example hydrophilic polyurethane may be coated with a solution or suspension of the adhesive in a volatile component and rapidly heating to produce the porous form. The method of British Patent Specification No. 1563695 may be employed with advantage. The coated films may then be cut, packaged and sterilized in conventional manner, for example by irradiation, heat or ethylene oxide.

The area of the pores in the adhesive layer may be varied by varying the ratio of water to lower boiling solvent in the emulsion and the drying temperature and the amount of time after spreading before entering the drying oven. In general the more important parameter is the length of time after spreading and before drying which is generally between 30 seconds and 2.5 minutes, more aptly between 45 seconds and 1.5 minutes, for example about 1 minute.

In a favoured aspect this invention provides a dressing as hereinbefore described in sterile form. Most aptly the sterile dressing is packaged in a bacteria-proof package such as a paper or aluminium foil pouch.

Suitable polyurethane may be produced by the methods of British Patent Specification No. 2093190A and incorporated herein by cross reference are page 6 line 35 to page 8 line 41 thereof.

Normally the dressings are provided for use with silicone release paper to protect the adhesive which protector is removed prior to use of the dressing.

The following Examples illustrate the invention:

DESCRIPTION

"Dry" MVP Determination

Discs of the material under test are clamped over Payne Permeability Cups (flanged metal cups) using sealing rings and screw clamps. The exposed surface area of the test sample is 10 cm². Each cup contains approximately 10 ml. of distilled water.

After weighing the cups are placed in a fan assisted electric oven which is maintained at 37°±1° C. The relative humidity within the oven is maintained at approximately 10% by placing 1 Kg. of anhydrous 3-8 mesh calcium chloride on the floor of the oven.

The cups are removed after 24 hours, allowed to cool for 20 minutes and re-weighed. The MVP of the test material is calculated from the weight loss and expressed in units of grams of weight per square meter per 24 hours.

"Wet" MVP determination

The method described above is employed except that the Payne Cups are inverted in the oven so that the water within the cups is in contact with the test material.

Demonstration 2

A solution of a hydrophilic polyurethane (of Example 2 of UK No. 2093190A) in industrial methylated spirits (18% solids) was cast using a doctor blade onto a silicone treated release paper (Steralease 50) to produce a coating weight after drying of 30±3 g/m². The cast film was dried at 80° C. to remove solvent.

EXAMPLE 1

An emulsion was prepared by high shear mixing of a polyvinyl ethyl ether adhesive (ex Union Carbide) (25%), petroleum spirit (40/60) (25%) and water (50%). This emulsion was coated onto a silicone release paper (Steralease 77) using a doctor blade and dried after 1 minute in a tunnel at 85° C. to give an adhesive coating of 30 gsm. The dried adhesive was laminated to a film of hydrophilic polyurethane (of Demonstration 2) using the minimum nip pressure between the rollers (about 20 psi gauge) at room temperature.

The laminate was cut into 10 cm × 15 cm portions as sealed into bacteria proof pouches and sterilised with ethylene oxide.

The dry-MVP of the dressing was approximately 1590 g/m² and the wet-MVP of the dressing was approximately 4750 g/m².

EXAMPLE 2

The procedure of Example 1 was followed except that the adhesive emulsion was composed of Primal N 580 (50/50 water/acrylic polymer emulsion ex Rohm & Haas) (80%) and petroleum spirit (40/60). The dry-MVP of the dressing was approximately 1300 g/m² and the wet-MVP of the dressing was approximately 5250 g/m².

EXAMPLE 3

A porous vinyl ether adhesive layer was applied to the film of Demonstration 2 as follows. The polyurethane film supported on its release paper was coated with an emulsion prepared by high shear mixing of polyvinyl ethyl ether adhesive (33%) (ex BASF), petroleum spirit (40/60) (17%) and water (50%). The coating was achieved using a doctor blade and after 1 minute the emulsion was dried at 85° C. in a tunnel to give a coating weight of 30 gsm.

The dry-MVP of the dressing was approximately 1800 g/m² and the wet-MVP of the dressing was approximately 4550 g/m².

EXAMPLE 4

The procedure of Example 1 was repeated using 22 gsm of adhesive. The dry-MVP of the dressing was approximately 1650 g/m² and the wet-MVP of the dressng was approximately 5100 g/m².

What we claim is:

1. A surgical dressing which consists essentially of a film which carries an adhesive layer for securing the dressing to the human body, wherein,
   (a) the film is continuous and comprises a polyurethane polyether polyamide block copolymer or a polyether polyester block copolymer which in contact with water has a higher MVP than when in contact with moisture vapor but not water,
   (b) the adhesive layer is porous such that the pores account for 10% to 50% of the area of the adhesive, and the adhesive allows access of water to the film when water is in contact with the adhesive layer so that,
   (c) said surgical dressing has an MVP of not less than 2500 g/m² when the adhesive layer is in contact with water and has an MVP of not more than 2000 g/m² when the adhesive layer is in contact with moisture vapor but not water; whereby the dressing is suitable for use on exuding wounds and non-exuding wounds.

2. A dressing according to claim 1 wherein the MVP is not more than 1500 g/m² when the adhesive layer is in contact with moisture vapour but not water.

3. A dressing according to claim 1 wherein the MVP is not less than 3200 g/m² when the adhesive layer is in contact with water.

4. A dressing according to claim 1 wherein the film comprises a hydrophilic polyurethane which when hydrated contains 5% to 50% of water and is from 15 to 80 microns thick.

5. A dressing according to claim 4 wherein the film comprises a hydrophilic polyurethane which when hydrated contains 10% to 40% of water and is from 20 to 60 microns thick.

6. A dressing according to claim 5 wherein the film is a hydrophilic polyurethane which is a hydrophilic polyether polyurethane.

7. A dressing according to claim 1 wherein the adhesive comprises a polyvinyl ethyl ether or an acrylate surgical adhesive.

8. A dressing according to claim 1 in which the average weight per unit area of adhsive is 20 g/m² to 45 g/m².

9. A dressing according to claim 1 in sterile form packaged in a bacteria proof package.

10. A surgical dressing according to claim 1 which also comprises a protector over the adhesive which is to be removed prior to the use of the dressing.

11. A surgical dressing acording to claim 10 wherein the protector is a silicone coated release paper.

12. A surgical dressing according to claim 1 for covering burns.

13. A surgical dressing according to claim 1 for covering donor sites.

14. A surgical dressing according to claim 1 for covering intravenous catheter sites.

15. A surgical dressing according to claim 1 wherein the film is a polyurethane.

16. A surgical dressing according to claim 1 wherein the film is a polyether polyamid block copolymer.

17. A surgical dressing according to claim 1 wherein the film is a polyether polyester block copolymer.

18. A surgical dressing according to claim 1 wherein the adhesive is an acrylic adhesive.

19. A surgical dressing according to claim 1 wherein the adhesive is an emulsion adhesive.

* * * * *